US012182974B2

(12) United States Patent
Nakamura

(10) Patent No.: US 12,182,974 B2
(45) Date of Patent: Dec. 31, 2024

(54) ENDOSCOPIC SURGERY SYSTEM, IMAGE PROCESSING APPARATUS, AND IMAGE PROCESSING METHOD

(71) Applicant: SONY GROUP CORPORATION, Tokyo (JP)

(72) Inventor: Yukihiro Nakamura, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 377 days.

(21) Appl. No.: 17/627,738

(22) PCT Filed: Jul. 15, 2020

(86) PCT No.: PCT/JP2020/027510
§ 371 (c)(1),
(2) Date: Jan. 17, 2022

(87) PCT Pub. No.: WO2021/020132
PCT Pub. Date: Feb. 4, 2021

(65) Prior Publication Data
US 2022/0261967 A1 Aug. 18, 2022

(30) Foreign Application Priority Data
Jul. 29, 2019 (JP) .................................. 2019-138534

(51) Int. Cl.
*G06T 5/73* (2024.01)
*A61B 1/00* (2006.01)
*G06T 7/246* (2017.01)

(52) U.S. Cl.
CPC .......... *G06T 5/73* (2024.01); *A61B 1/000095* (2022.02); *G06T 7/246* (2017.01);
(Continued)

(58) Field of Classification Search
CPC ............ G06T 5/73; G06T 2207/10068; G06T 2207/20201; G06T 7/246;
(Continued)

(56) References Cited

U.S. PATENT DOCUMENTS

2007/0161853 A1* 7/2007 Yagi ....................... A61B 1/041
600/117
2017/0206640 A1* 7/2017 Ichiki ................. A61B 1/00154

FOREIGN PATENT DOCUMENTS

JP 2012-239644 A 12/2012
JP 2016000065 A 1/2016
(Continued)

OTHER PUBLICATIONS

International Search Report and Written Opinion of PCT Application No. PCT/JP2020/027510, issued on Sep. 15, 2020, 09 pages of ISRWO.

*Primary Examiner* — Ajibola A Akinyemi
(74) *Attorney, Agent, or Firm* — CHIP LAW GROUP

(57) ABSTRACT

The present disclosure relates to an endoscopic surgery system, an image processing apparatus, and an image processing method that enable better endoscopic observation. Motion components at the time of imaging are estimated on the basis of an image captured by an endoscope, a degree of reliability indicating a degree that the motion components are motion components for the entire image is set, and a correction amount used when correction processing of correcting a blur is performed on the image is controlled according to the degree of reliability. For example, in a case where the motion components are single motion components, the degree of reliability is set to 1.0, and in a case where the motion components are a plurality of motion components, the degree of reliability is set to 0.0. The (Continued)

present technology can be applied to, for example, an endoscopic surgery system used in surgery using an endoscope.

15 Claims, 10 Drawing Sheets

(52) U.S. Cl.
CPC ............... *G06T 2207/10068* (2013.01); *G06T 2207/20201* (2013.01); *G06T 2207/30004* (2013.01)

(58) Field of Classification Search
CPC . G06T 2207/10012; G06T 2207/10056; G06T 2207/30096; G06T 5/20; G06T 7/20; G06T 2207/10016; G06T 2207/20081; G06T 2207/20084
USPC ........................................................ 382/128
See application file for complete search history.

(56) References Cited

FOREIGN PATENT DOCUMENTS

| | | |
|---|---|---|
| WO | WO-2005077253 A | 8/2005 |
| WO | 2018/168261 A1 | 9/2018 |
| WO | 2019/013217 A1 | 1/2019 |

* cited by examiner

ENDOSCOPIC SURGERY SYSTEM, IMAGE PROCESSING APPARATUS, AND IMAGE PROCESSING METHOD

CROSS REFERENCE TO RELATED APPLICATIONS

This application is a U.S. National Phase of International Patent Application No. PCT/JP2020/027510 filed on Jul. 15, 2020, which claims priority benefit of Japanese Patent Application No. JP 2019-138534 filed in the Japan Patent Office on Jul. 29, 2019. Each of the above-referenced applications is hereby incorporated herein by reference in its entirety.

TECHNICAL FIELD

The present disclosure relates to an endoscopic surgery system, an image processing apparatus, and an image processing method, and particularly to an endoscopic surgery system, an image processing apparatus, and an image processing method that enable better endoscopic observation.

BACKGROUND ART

In recent years, in medical sites, an endoscopic surgery system capable of performing surgery while observing an affected part with an endoscope is used instead of a conventional abdominal operation.

For example, Patent Document 1 discloses an endoscopic apparatus that performs blur correction processing according to motion information of an imaging visual field according to an operation of moving the imaging visual field of an imaging unit and a motion between a plurality of images acquired in time series.

CITATION LIST

Patent Document

Patent Document 1: JP 2012-239644 A

SUMMARY OF THE INVENTION

Problems to be Solved by the Invention

However, in the endoscopic apparatus disclosed in Patent Document 1 described above, for example, in a case where a ratio between motion components of the imaging unit and motion components of a medical instrument or the like other than the imaging unit is close, it is difficult to correctly estimate motion components included in an image. Thus, the blur correction processing is performed on the basis of an erroneously estimated motion, and as a result, there is a concern that distortion occurs in an image obtained by performing the blur correction processing, and it is assumed that good observation cannot be performed in such an image.

The present disclosure has been made in view of such a situation, and enables better endoscopic observation.

Solutions to Problems

An endoscopic surgery system and an image processing apparatus of an aspect of the present disclosure includes: a motion estimation unit that estimates motion components at a time of imaging on the basis of an image captured by an endoscope, and sets a degree of reliability indicating a degree that the motion components are motion components for the entire image; and a correction amount control unit that controls, according to the degree of reliability, a correction amount used when correction processing of correcting a blur is performed on the image.

An image processing method of an aspect of the present disclosure is performed by an image processing apparatus, the image processing method including: estimating motion components at a time of imaging on the basis of an image captured by an endoscope, and setting a degree of reliability indicating a degree that the motion components are motion components for the entire image; and controlling, according to the degree of reliability, a correction amount used when correction processing of correcting a blur is performed on the image.

In an aspect of the present disclosure, motion components at the time of imaging are estimated on the basis of an image captured by an endoscope, a degree of reliability indicating a degree that the motion components are motion components for the entire image is set, and a correction amount used when correction processing is performed on the image is controlled according to the degree of reliability.

MODE FOR CARRYING OUT THE INVENTION

Hereinafter, specific embodiments to which the present technology is applied will be described in detail with reference to the drawings.

<Configuration Example of Endoscopic Surgery System>

Figure 1:
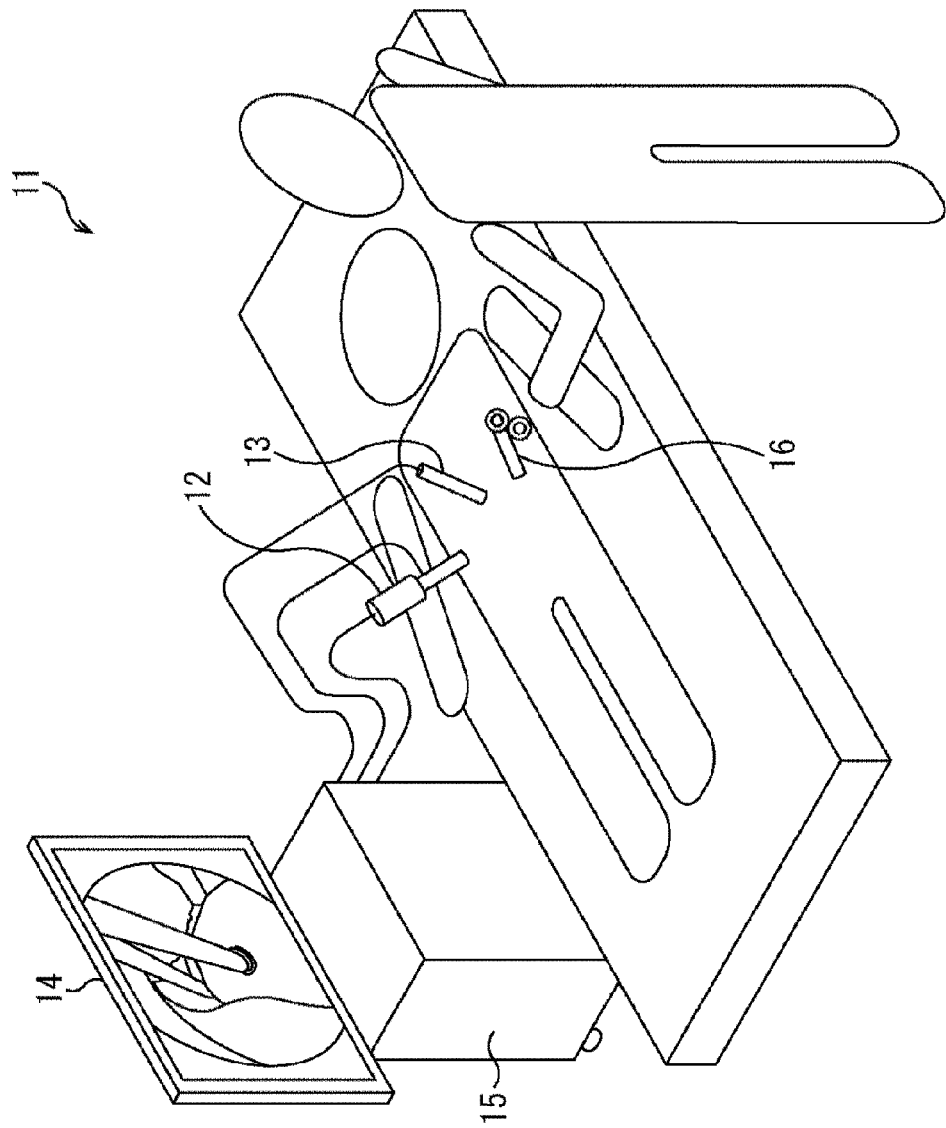
FIG. 1 is a diagram illustrating a configuration example of an embodiment of an endoscopic surgery system to which the present technology is applied.

FIG. 1 is a block diagram illustrating a configuration example of an embodiment of an endoscopic surgery system to which the present technology is applied.

An endoscopic surgery system 11 illustrated in FIG. 1 includes an endoscope 12, an energy treatment tool 13, a display device 14, and a device unit 15.

For example, in surgery using the endoscopic surgery system 11, the endoscope 12 and the energy treatment tool 13 are inserted into the body of a patient, and a forceps 16 is inserted into the body of the patient. Then, in the endoscopic surgery system 11, an image of an affected part such as a tumor captured by the endoscope 12 is displayed on the display device 14 in real time, and a surgeon can treat the affected part by using the energy treatment tool 13 and the forceps 16 while viewing the image.

The endoscope 12 is configured by, for example, attaching a cylindrical lens barrel portion in which an optical system such as an objective lens is incorporated to a camera head including an image sensor and the like.

The energy treatment tool 13 is, for example, a medical instrument used in endoscopic surgery for excision of an affected part or sealing of a blood vessel by heat generated by a high-frequency current.

The display device 14 displays an image obtained by performing image processing in the device unit 15 on an image captured by the endoscope 12.

The device unit 15 includes an image processing apparatus (FIG. 2) that performs image processing on an image captured by the endoscope 12, and also includes various devices necessary for performing surgery using the endoscopic surgery system 11. For example, a camera control unit (CCU) that controls imaging by the endoscope 12, a light source device that supplies light irradiated to an affected part when the endoscope 12 performs imaging, a treatment tool device that supplies a high-frequency current necessary for treatment of the affected part by the energy treatment tool 13, and the like are incorporated in the device unit 15.

In the endoscopic surgery system 11 configured as described above, in the device unit 15, for example, image processing of appropriately correcting a blur occurring in an image captured by the endoscope 12 is performed, and the image in which the blur is appropriately corrected is displayed on the display device 14. Therefore, in surgery using the endoscopic surgery system 11, a surgeon or the like can treat an affected part while observing by the image in which the blur is appropriately corrected.

<Configuration Example of Image Processing Apparatus>

Figure 2:
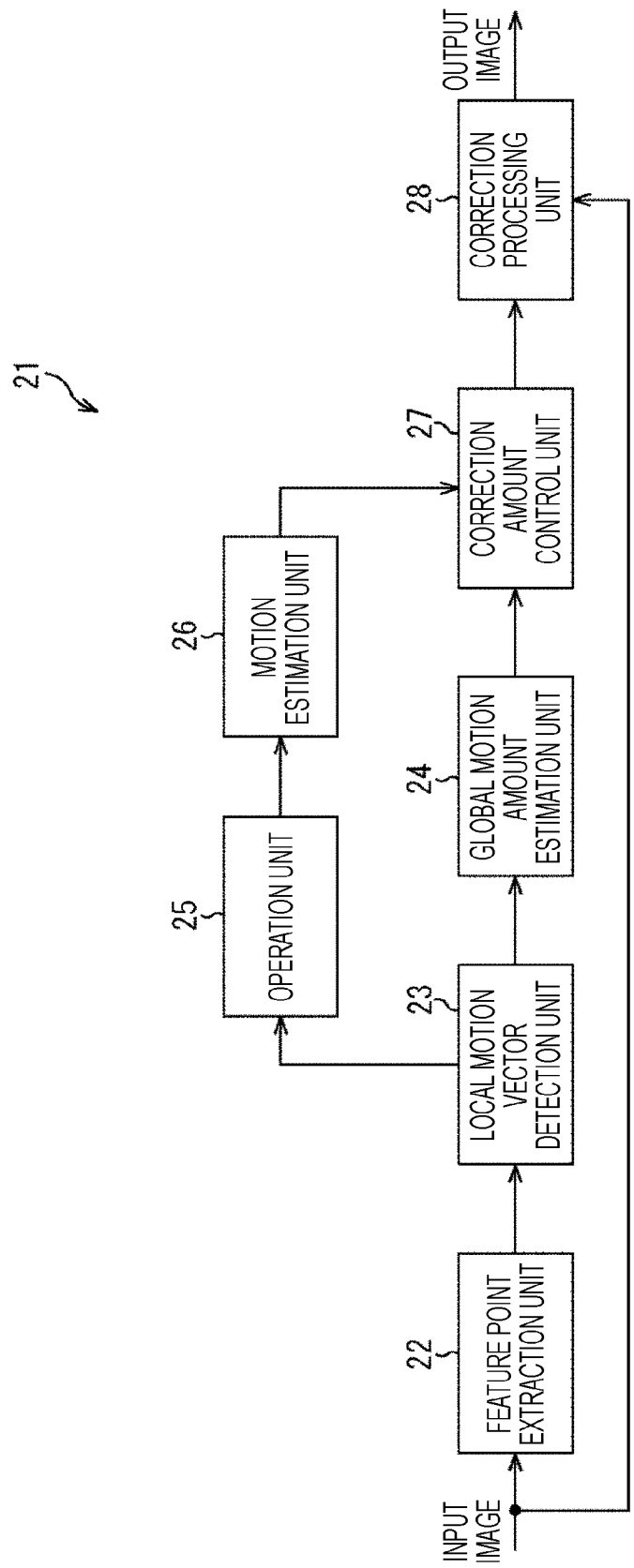
FIG. 2 is a block diagram illustrating a configuration example of an image processing apparatus.

FIG. 2 is a block diagram illustrating a configuration example of the image processing apparatus 21 included in the device unit 15.

As illustrated in FIG. 2, the image processing apparatus 21 includes a feature point extraction unit 22, a local motion vector detection unit 23, a global motion amount estimation unit 24, an operation unit 25, a motion estimation unit 26, a correction amount control unit 27, and a correction processing unit 28.

In addition, an image captured by the endoscope 12 of FIG. 1 is input to the image processing apparatus 21. In this image, an overall motion (overall blur) due to movement of the endoscope 12 may occur, and in a case where the energy treatment tool 13, the forceps 16, or the like is imaged by the endoscope 12, a local motion (local blur) due to movement of the energy treatment tool 13, the forceps 16, or the like may occur.

The feature point extraction unit 22 extracts a feature point to be a point indicating a portion to be a feature in the image captured by the endoscope 12, and supplies a plurality of the extraction points extracted from the image to the local motion vector detection unit 23.

The local motion vector detection unit 23 detects a local motion vector indicating a motion occurring in a local portion of an image on the basis of a motion of each of the plurality of feature points supplied from the feature point extraction unit 22. Then, the local motion vector detection unit 23 supplies a plurality of the local motion vectors detected from the image captured by the endoscope 12 of FIG. 1 to the global motion amount estimation unit 24 and the operation unit 25.

The global motion amount estimation unit 24 estimates a global motion amount representing magnitude of an overall motion of the image on the basis of the plurality of local motion vectors supplied from the local motion vector detection unit 23, and supplies the estimated global motion amount to the correction amount control unit 27.

The operation unit 25 performs operation based on the plurality of local motion vectors supplied from the local motion vector detection unit 23. For example, the operation unit 25 performs operation to obtain a norm and an angle of each local motion vector. Then, the operation unit 25 calculates a standard deviation (hereinafter, referred to as norm standard deviation of a local motion vector group) indicating a degree of dispersion of the norm of each local motion vector, and supplies the standard deviation to the motion estimation unit 26. Furthermore, the operation unit 25 calculates a standard deviation (hereinafter, referred to as angle standard deviation of the local motion vector group) indicating a degree of dispersion of the angle of each local motion vector, and supplies the standard deviation to the motion estimation unit 26.

According to the norm standard deviation and the angle standard deviation of the local motion vector group calculated by the operation unit 25, the motion estimation unit 26 estimates motion components at the time of imaging on the basis of the image to be processed in image processing, with reference to a threshold curve th illustrated in FIG. 3 as described later. That is, the motion estimation unit 26 estimates which of a single motion component and a plurality of motion components is included in the image. For example, in a case where motion components included in the image to be processed are largely occupied by motion components of a single size and direction, it is estimated that the image includes a single motion component. On the other hand, in a case where motion components included in the image to be processed are largely occupied by motion components of a plurality of different sizes and directions, it is estimated that the image includes a plurality of motion components. Then, according to the estimation result of the motion components, the motion estimation unit 26 sets a degree of reliability indicating a degree to which the motion components included in the image are trusted to be caused by the motion of the entire image as a result of the movement of the endoscope 12, and supplies the degree of reliability to the correction amount control unit 27.

For example, according to the estimation result of the motion components, in a case where a single motion component is included in the image to be processed, the motion estimation unit 26 sets the degree of reliability to 1.0 on the assumption that the degree to which the motion components included in the image are caused by the motion of the entire image is large. On the other hand, according to the estimation result of the motion components, in a case where a plurality of motion components is included in the image to be processed, the motion estimation unit 26 sets the degree of reliability to 0.0 on the assumption that the degree to which the motion components included in the image are caused by the motion of the entire image is small and are caused by, for example, a motion of the energy treatment tool 13, the forceps 16, or the like. Note that each degree of reliability is not limited to 0.0 or 1.0, and for example, an optional value between 0.0 and 1.0 may be used.

The correction amount control unit 27 controls the global motion amount supplied from the global motion amount estimation unit 24 according to the degree of reliability supplied from the motion estimation unit 26, and obtains a correction amount used when the correction processing unit 28 performs correction processing of correcting a blur on the image to be processed. For example, in a case where the degree of reliability supplied from the motion estimation unit 26 is 1.0, the correction amount control unit 27 uses the global motion amount as it is as the correction amount, and supplies the correction amount to the correction processing unit 28. On the other hand, in a case where the degree of reliability supplied from the motion estimation unit 26 is 0.0, the correction amount control unit 27 does not use the global motion amount as the correction amount, sets the correction amount to 0, and supplies the correction amount to the correction processing unit 28.

The correction processing unit 28 performs the correction processing of correcting a blur occurring in the image to be processed input to the image processing apparatus 21 with the correction amount according to the control by the correction amount control unit 27, and outputs a resultant image to the display device 14. For example, when the correction amount in which the global motion amount is controlled according to the degree of reliability is supplied from the correction amount control unit 27, the correction processing unit 28 corrects a blur of the image by performing smoothing so as to apply a filter in a time direction according to the correction amount. Thus, for example, in a case where the correction amount supplied from the correction amount control unit 27 is 0, the correction processing unit 28 outputs the image as it is without performing the correction processing on the image to be processed.

That is, the correction processing unit 28 performs the correction processing of correcting a blur according to the global motion amount in a case where a single motion component is included in the image to be processed, and turns off the correction processing in a case where a plurality of motion components is included in the image to be processed.

The image processing apparatus 21 configured as described above can appropriately perform the correction processing depending on whether the motion components included in the image to be processed are single motion components or a plurality of motion components. For example, in a case where the degree to which the motion components included in the image to be processed are caused by the motion of the entire image is large, the image processing apparatus 21 can output an image in which the overall blur occurring in the image due to the motion of the endoscope 12 is corrected.

Furthermore, in a case where the degree to which the motion components included in the image to be processed are caused by the motion of the entire image is small and a degree of a local blur in the image is large, the image processing apparatus 21 can avoid performing inappropriate correction processing. For example, in a case where the degree to which the motion components are local due to a motion of the energy treatment tool 13, the forceps 16, or the like is large, an influence of the local blur is strongly received at the time of estimation of the global motion amount. At this time, since the estimated global motion amount does not correctly reflect the overall blur, distortion occurs not only in a region of the local blur but also in the correction result as a whole.

Thus, in a case where the degree to which the motion components included in the image to be processed are caused by a plurality of motions is large, the image processing apparatus 21 can avoid occurrence of distortion not only in the region of the local blur but also in the correction result as a whole. That is, in a case where a plurality of motion components is included in the image, the correction processing of correcting a blur according to the global motion amount is not performed, and thus, it is possible to avoid performing inappropriate correction processing.

Therefore, a surgeon performing surgery can perform observation using an image in which an overall blur generated by movement of the endoscope 12 itself is corrected, can avoid observation using an image with distortion generated when a local blur generated by a motion of the energy treatment tool 13, the forceps 16, or the like is corrected, and can perform better endoscopic observation with good image quality without discomfort.

Here, estimation of motion components by the motion estimation unit 26 will be described with reference to FIG. 3.

As described above, the norm standard deviation and the angle standard deviation of the local motion vector group calculated by the operation unit 25 are supplied to the motion estimation unit 26. Then, in the motion estimation unit 26, the threshold curve th indicating a threshold for estimating which of a single motion component and a plurality of motion components is included in the image to be processed is set.

Figure 3:
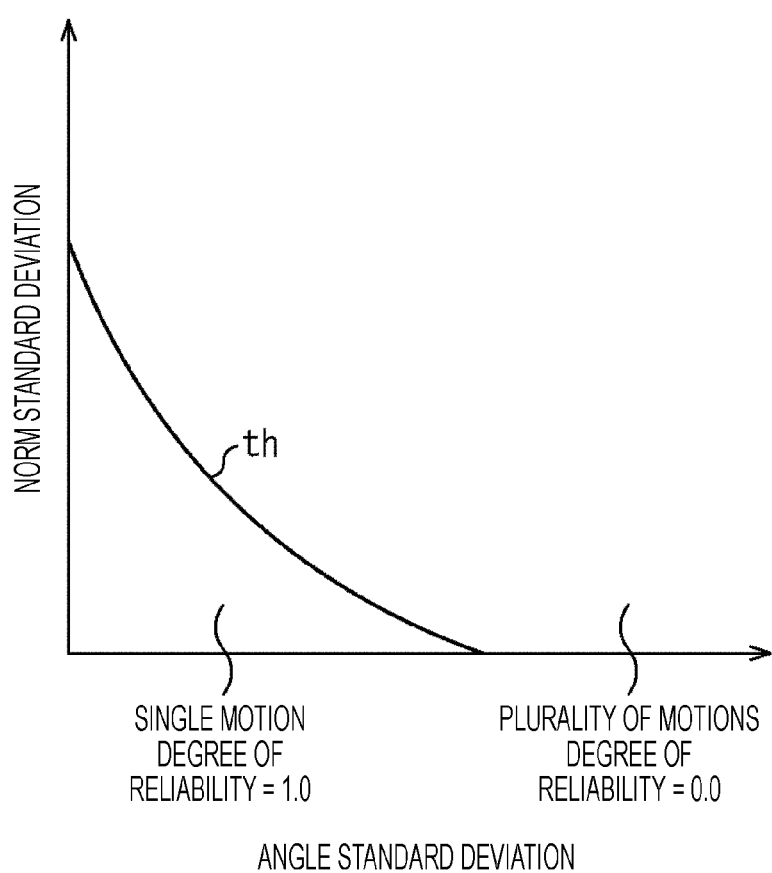
FIG. 3 is a diagram illustrating a first example of a threshold curve referred to in estimation of motion components.

In FIG. 3, a vertical axis indicates the norm standard deviation of the local motion vector group, and a horizontal axis indicates the angle standard deviation of the local motion vector group, and the threshold curve th as illustrated is set. For example, the threshold curve th is represented by a curve in which the angle standard deviation decreases as the norm standard deviation increases and the angle standard deviation increases as the norm standard deviation decreases, and the curve protrudes in a direction in which the norm standard deviation and the angle standard deviation decrease.

That is, when a single motion component is included in the image, the local motion vector group tends to have a certain size and direction, so that the norm standard deviation and the angle standard deviation decrease. On the other hand, when a plurality of motion components is included in the image, the local motion vectors are divided into a plurality of groups indicating different directions, so that the norm standard deviation and the angle standard deviation increase.

Thus, in a case where the norm standard deviation and the angle standard deviation of the local motion vector group obtained from the image to be processed are in a region less than the threshold curve th illustrated in FIG. 3 (that is, a region closer to the origin than the threshold curve th), the motion estimation unit 26 can estimate that the image includes a single motion component. On the other hand, in a case where the norm standard deviation and the angle standard deviation of the local motion vector group obtained from the image to be processed are in a region equal to or larger than the threshold curve th illustrated in FIG. 3, the motion estimation unit 26 can estimate that the image includes a plurality of motion components.

Therefore, for the plurality of local motion vectors obtained from the image to be processed, in a case where the degree of dispersion of the norm is small and the degree of dispersion of the angle is small, it is estimated that the image to be processed includes a single motion component, and the degree of reliability is set to 1.0. On the other hand, for the plurality of local motion vectors obtained from the image to be processed, in a case where the degree of dispersion of the norm is large and the degree of dispersion of the angle is large, it is estimated that the image to be processed includes a plurality of motion components, and the degree of reliability is set to 0.0.

<First Processing Example of Image Processing>

Figure 4:
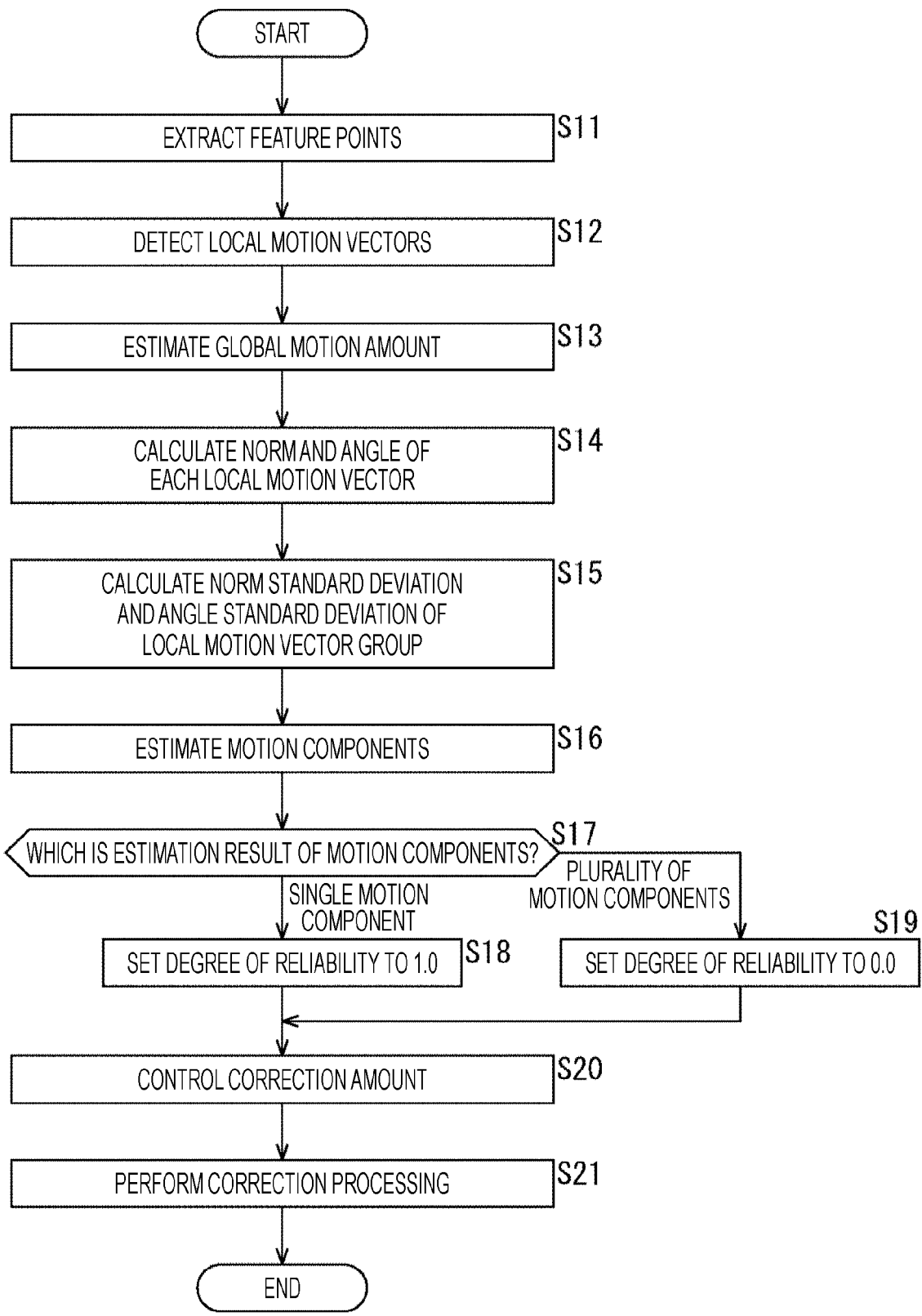
FIG. 4 is a flowchart illustrating a first processing example of image processing.

FIG. 4 is a flowchart illustrating a first processing example of the image processing executed in the image processing apparatus 21.

For example, when an image captured by the endoscope 12 is input to the image processing apparatus 21, the image processing is started by using the image as an image to be processed. In Step S11, the feature point extraction unit 22 extracts a plurality of feature points from the image to be processed.

In Step S12, the local motion vector detection unit 23 detects a plurality of local motion vectors from the image to be processed according to the plurality of feature points extracted by the feature point extraction unit 22 in Step S11.

In Step S13, the global motion amount estimation unit 24 estimates a global motion amount from the image to be processed according to the plurality of local motion vectors detected by the local motion vector detection unit 23 in Step S12.

In Step S14, the operation unit 25 calculates a norm and an angle of each local motion vector for the plurality of local motion vectors detected by the local motion vector detection unit 23 in Step S12.

In Step S15, the operation unit 25 calculates a norm standard deviation of the local motion vector group on the basis of the norm of each local motion vector, and calculates an angle standard deviation of the local motion vector group on the basis of the angle of each local motion vector.

In Step S16, according to the norm standard deviation and the angle standard deviation of the local motion vector group calculated by the operation unit 25 in Step S15, the motion estimation unit 26 estimates motion components included in the image to be processed with reference to the threshold curve th illustrated in FIG. 3 described above.

In Step S17, the motion estimation unit 26 determines whether the estimation result of the motion components in Step S16 is a single motion component or a plurality of motion components.

In a case where the motion estimation unit 26 determines that the estimation result of the motion components is a single motion component in Step S17, the processing proceeds to Step S18. Then, in Step S18, the motion estimation unit 26 sets a degree of reliability to 1.0.

On the other hand, in a case where the motion estimation unit 26 determines that the estimation result of the motion components is a plurality of motion components in Step S17, the processing proceeds to Step S19. Then, in Step S19, the motion estimation unit 26 sets the degree of reliability to 0.0.

After the processing of Step S18 or S19, the processing proceeds to Step S20, in which the correction amount control unit 27 controls a correction amount based on the global motion amount estimated by the global motion amount estimation unit 24 in Step S13 according to the degree of reliability set by the motion estimation unit 26.

In Step S21, the correction processing unit 28 performs correction processing of correcting a blur on the image to be processed with the correction amount controlled by the correction amount control unit 27 in Step S20. That is, in a case where the degree of reliability set by the motion estimation unit 26 is 1.0, the correction processing of correcting a blur with the correction amount based on the global motion amount is performed, and in a case where the degree of reliability set by the motion estimation unit 26 is 0.0, the correction processing is turned off. Then, after the correction processing unit 28 outputs an image obtained by performing the correction processing or the image in which the correction processing is turned off to the display device 14, the processing is terminated.

As described above, the image processing apparatus 21 can appropriately perform (switch on/off of) the correction processing of correcting a blur in the image by determining which of a single motion component and a plurality of motion components is included in the image to be processed. With this configuration, it is possible to output an image in which the blur is corrected in a case where a single motion component is included in the image to be processed, and it is possible to output an image in which the blur is not corrected (on which performing inappropriate correction processing is avoided) in a case where a plurality of motion components is included in the image to be processed.

<Second Processing Example of Image Processing>

A second processing example of the image processing executed in the image processing apparatus 21 will be described with reference to FIGS. 5 to 7.

In the first processing example of the image processing described above, in the image processing apparatus 21, the degree of reliability is set to 0.0 or 1.0 according to the threshold curve th illustrated in FIG. 3, and on/off switching of the image processing of correcting a blur is performed. On the other hand, in the second processing example of the image processing, it is possible to adjust intensity of correcting a blur by providing a transition zone in which the degree of reliability transitions from 0.0 to 1.0.

Figure 5:
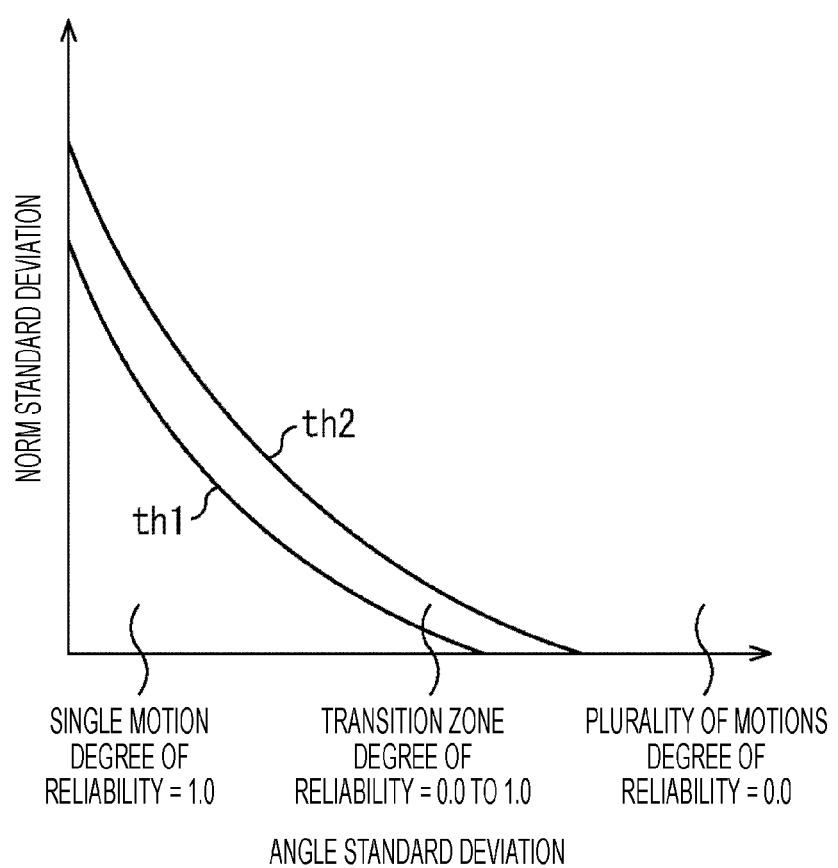
FIG. 5 is a diagram illustrating a second example of the threshold curve referred to in the estimation of the motion components.

That is, as illustrated in FIG. 5, a first threshold curve th1 and a second threshold curve th2 are set. The first threshold curve th1 indicates a threshold for estimating whether or not a single motion component is included in the image to be processed, and the second threshold curve th2 indicates a threshold for estimating whether or not a plurality of motion components is included in the image to be processed.

Therefore, in a case where the norm standard deviation and the angle standard deviation of the local motion vector group obtained from the image to be processed are in a region less than the first threshold curve th1, the motion estimation unit 26 estimates that the image includes a single motion component and sets the degree of reliability to 1.0. On the other hand, in a case where the norm standard deviation and the angle standard deviation of the local motion vector group obtained from the image to be processed are in a region larger than the second threshold curve th2, the motion estimation unit 26 estimates that the image includes a plurality of motion components and sets the degree of reliability to 0.0.

In addition, in a case where the norm standard deviation and the angle standard deviation of the local motion vector group obtained from the image to be processed are in a region equal to or larger than the first threshold curve th1 and equal to or smaller than the second threshold curve th2, the motion estimation unit 26 assumes that the norm standard deviation and the angle standard deviation are in a transition zone between a single motion component and a plurality of motion components and sets the degree of reliability between 0.0 to 1.0.

Figure 6:
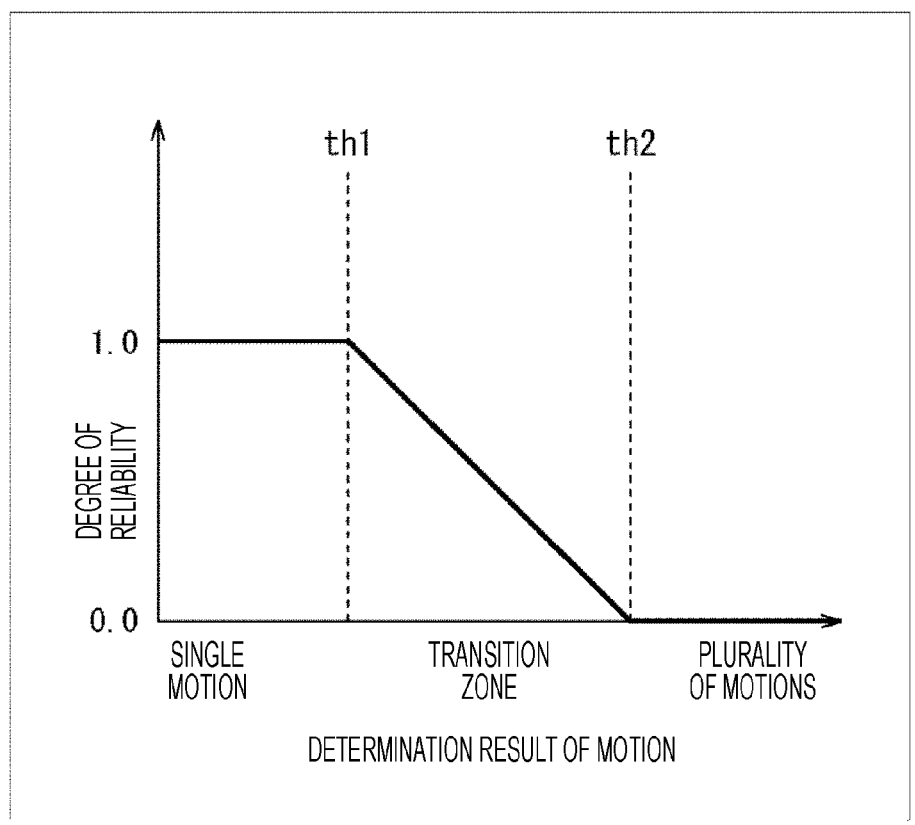
FIG. 6 is a diagram for describing a degree of reliability obtained in a transition zone.

For example, as illustrated in FIG. 6, the motion estimation unit 26 can obtain the degree of reliability in the transition zone so that the degree of reliability linearly decreases according to values of the norm standard deviation and the angle standard deviation of the local motion vector group from the degree of reliability 1.0 at the time of the first threshold curve th1 to the degree of reliability 0.0 at the time of the second threshold curve th2.

Then, the correction amount control unit 27 can control a correction amount according to the degree of reliability set by the motion estimation unit 26. For example, when the degree of reliability is set to 0.0 and 1.0, the correction amount control unit 27 controls the correction amount similarly to the first processing example of the image processing described above. In addition, when the degree of reliability is set between 0.0 and 1.0, the correction amount control unit 27 uses the degree of reliability to calculate a correction amount that interpolates between the time when the correction processing is on and the time when the correction processing is off. For example, the correction amount control unit 27 may simply calculate a value obtained by multiplying the correction amount by the degree of reliability as the correction amount according to the motion components.

By using such a second processing example of the image processing, the image processing apparatus 21 can output an image with less discomfort.

For example, as in the first processing example of the image processing, in a case where control is performed in which the degree of reliability is set to 1.0 or 0.0 and on/off of the correction processing is switched, a frequency of on/off switching of the correction processing may increase. That is, in a case where the degree of reliability that changes with transition of a frame exists in the vicinity of the threshold curve th (FIG. 3) and the estimation result changes between a single motion component and a plurality of motion components for each frame or for each several frames, the frequency of on/off switching of the correction processing increases. In such a case, it is assumed that there is an adverse effect such as discomfort is generated by the image becoming laggy over time.

On the other hand, in the second processing example of the image processing, since the degree of reliability is set to values from 0.0 to 1.0 in the transition zone, it is possible to avoid an increase in the frequency of on/off switching of the correction processing, and it is possible to alleviate such an adverse effect and reduce discomfort.

Figure 7:
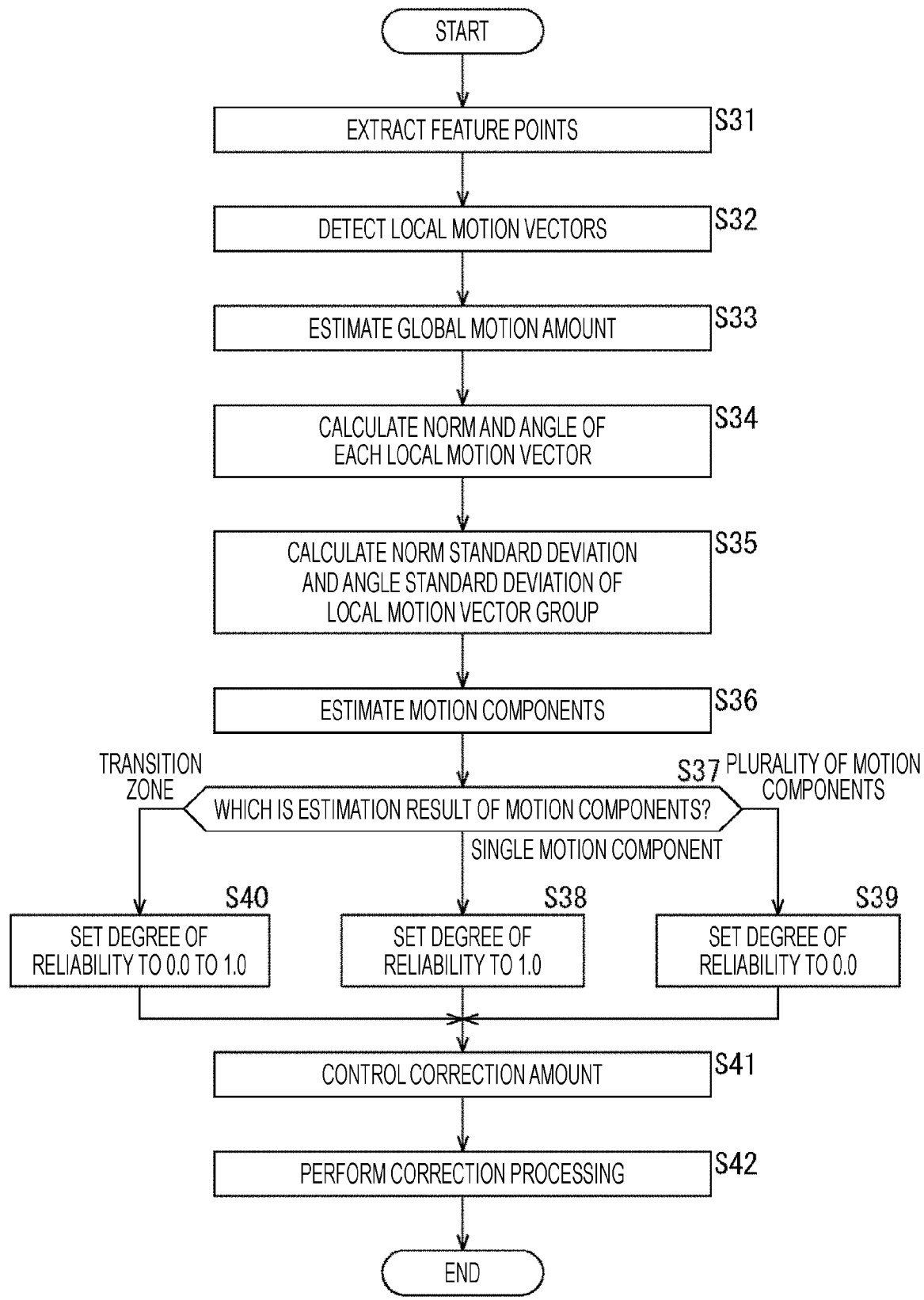
FIG. 7 is a flowchart illustrating a second processing example of the image processing.

FIG. 7 is a flowchart illustrating the second processing example of the image processing executed in the image processing apparatus 21.

In Steps S31 to S35, processing similar to that in Steps S11 to 15 in FIG. 4 is performed. Then, in Step S36, according to the norm standard deviation and the angle standard deviation of the local motion vector group calculated by the operation unit 25 in Step S35, the motion estimation unit 26 estimates motion components included in the image to be processed with reference to the first threshold curve th1 and the second threshold curve th2 illustrated in FIG. 5 described above.

In Step S37, the motion estimation unit 26 determines whether the estimation result of the motion components in Step S36 is a single motion component, a plurality of motion components, or a transition zone.

In a case where the motion estimation unit 26 determines that the estimation result of the motion components is a single motion component in Step S37, the processing proceeds to Step S38. Then, in Step S38, the motion estimation unit 26 sets the degree of reliability to 1.0.

On the other hand, in a case where the motion estimation unit 26 determines that the estimation result of the motion components is a plurality of motion components in Step S37, the processing proceeds to Step S39. Then, in Step S39, the motion estimation unit 26 sets the degree of reliability to 0.0.

On the other hand, in a case where the motion estimation unit 26 determines that the estimation result of the motion components is a transition zone in Step S37, the processing proceeds to Step S40. Then, in Step S40, the motion estimation unit 26 sets the degree of reliability to a value from 0.0 to 1.0 as illustrated in FIG. 6 described above.

After the processing of Step S38, S39, or S40, the processing proceeds to Step S41, in which the correction amount control unit 27 controls a correction amount based on the global motion amount estimated by the global motion amount estimation unit 24 in Step S33 according to the degree of reliability set by the motion estimation unit 26.

In Step S42, the correction processing unit 28 performs correction processing of correcting a blur on the image to be processed with the correction amount controlled by the correction amount control unit 27 in Step S41. That is, in a case where the degree of reliability set by the motion estimation unit 26 is 1.0, the correction processing of correcting a blur with the correction amount based on the global motion amount is performed, and in a case where the degree of reliability set by the motion estimation unit 26 is 0.0, the correction processing is turned off. Furthermore, in a case where the degree of reliability set by the motion estimation unit 26 is a value between 1.0 and 0.0, the correction processing of correcting a blur with the correction amount according to the degree of reliability is performed. Then, after the correction processing unit 28 outputs an image obtained by performing the correction processing or the image in which the correction processing is turned off to the display device 14, the processing is terminated.

As described above, the image processing apparatus 21 can appropriately perform the correction processing of correcting a blur in the image by determining whether a single motion component or a plurality of motion components is included in the image to be processed or it is a transition zone between the single motion component or the plurality of motion components. Therefore, the image processing apparatus 21 can alleviate the adverse effect caused by the switching between a single motion component and a plurality of motion components between the frames as described above, and can output an image in which discomfort is reduced.

Note that, in the image processing apparatus 21, the correction amount control unit 27 may accumulate the degree of reliability sequentially supplied from the motion estimation unit 26 and smooth the degrees of reliability in the time direction. Then, the correction amount control unit 27 can control, by using the degrees of reliability smoothed in the time direction, the correction amount so as to smoothly change. With this configuration, the image processing apparatus 21 can alleviate the adverse effect caused by the switching between a single motion component and a plurality of motion components between the frames as described above, and can output an image in which discomfort is further reduced.

Furthermore, in the image processing apparatus 21, the threshold curve th illustrated in FIG. 3 or the first threshold curve th1 or the second threshold curve th2 illustrated in FIG. 5 is not limited to the illustrated shape, and may be adjusted so that the motion components included in the image can be appropriately estimated. For example, the threshold curve can be adjusted according to characteristics (zoom magnification, diaphragm, and the like) of the endoscope 12, and can be adjusted according to a type, a situation, and the like of surgery in which the endoscope 12 is used. Moreover, the image processing apparatus 21 can be used for image processing on an image of a surgery system that does not use the endoscope 12, for example, an image captured by a surgical microscope.

As described above, the endoscopic surgery system 11 can display the image appropriately subjected to the correction processing of correcting a blur on the display device 14 by estimating the motion components at the time of imaging on the basis of the image to be processed. For example, the endoscopic surgery system 11 can correct the overall blur in a case where a motion of the endoscope 12 occupies a significant portion in a screen. Furthermore, for example, in a case where a motion of the energy treatment tool 13, the forceps 16, gauze, or the like, or a motion in a living body such as pulsation or respiratory motion occupies a significant portion in the screen, the endoscopic surgery system 11 can prevent occurrence of distortion due to the correction processing being performed in response to such motions.

Therefore, in the endoscopic surgery system 11, the image in which a blur is appropriately corrected is displayed on the display device 14, and a surgeon can satisfactorily observe an affected part by the image captured by the endoscope 12.

<Configuration Example of Computer>

Next, the series of processing (image processing method) described above can be performed by hardware or software. In a case where the series of processing is performed by software, a program constituting the software is installed in a general-purpose computer or the like.

Figure 8:
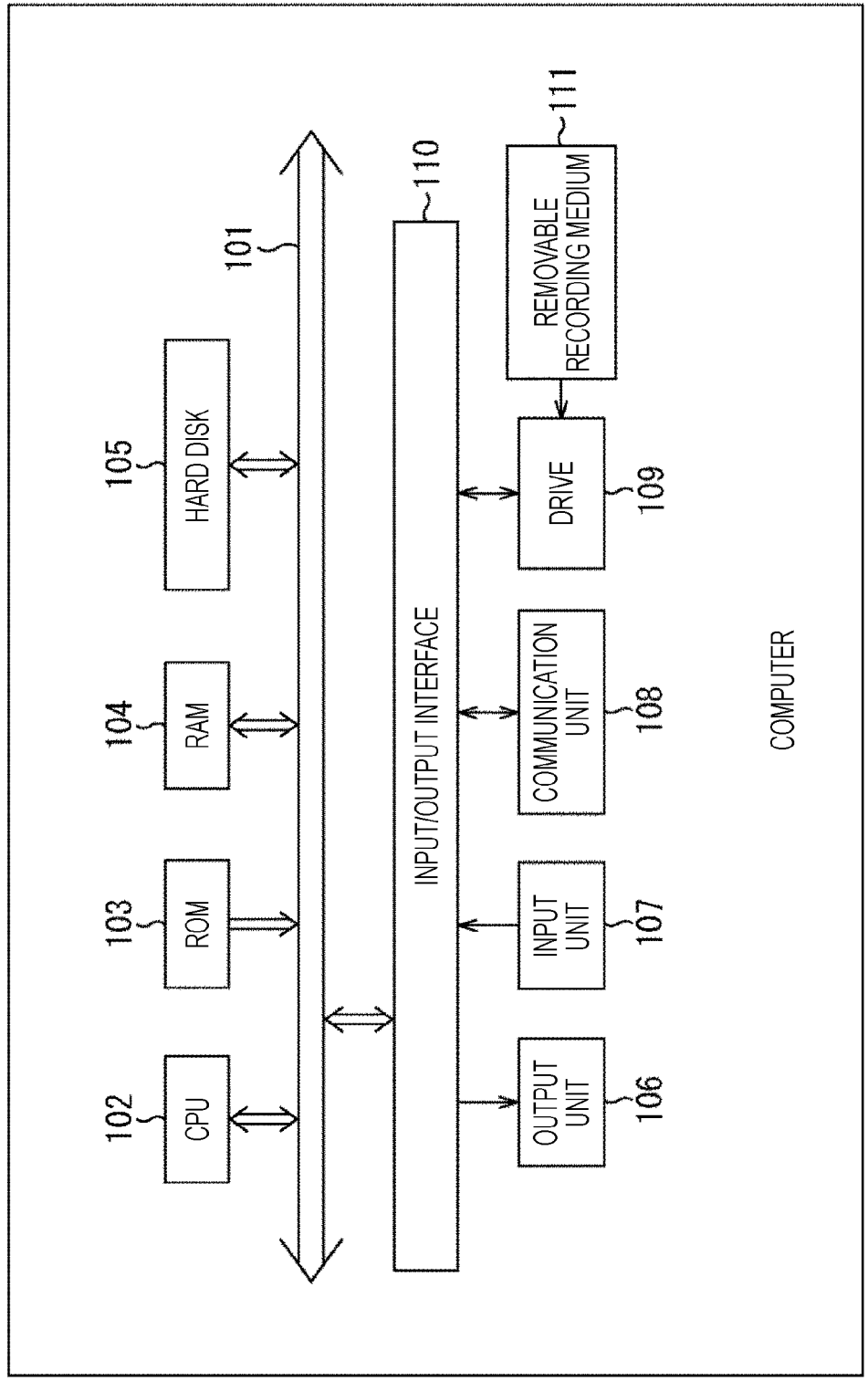
FIG. 8 is a block diagram illustrating a configuration example of an embodiment of a computer to which the present technology is applied.

FIG. 8 is a block diagram illustrating a configuration example of an embodiment of a computer in which a program that executes the series of processing described above is installed.

The program can be recorded in advance in a hard disk 105 or a ROM 103 serving as a recording medium incorporated in the computer.

Alternatively, the program can be stored (recorded) in a removable recording medium 111 driven by a drive 109. Such a removable recording medium 111 can be provided as so-called package software. Here, examples of the removable recording medium 111 include a flexible disk, a compact disc read only memory (CD-ROM), a magneto optical (MO) disk, a digital versatile disc (DVD), a magnetic disk, and a semiconductor memory.

Note that the program can be installed in the computer from the removable recording medium 111 as described above, or can be downloaded to the computer via a communication network or a broadcast network and installed in the hard disk 105 incorporated in the computer. That is, for example, the program can be wirelessly transferred from a download site to the computer via an artificial satellite for digital satellite broadcasting, or wiredly transferred to the computer via a network such as a local area network (LAN) and the Internet.

The computer incorporates a central processing unit (CPU) 102, and an input/output interface 110 is connected to the CPU 102 via a bus 101.

When a command is input by a user operating an input unit 107 via the input/output interface 110, or the like, the CPU 102 executes a program stored in the read only memory (ROM) 103 according to the command. Alternatively, the CPU 102 loads a program stored in the hard disk 105 into a random access memory (RAM) 104 and executes the program.

With this configuration, the CPU 102 performs the processing according to the flowcharts described above or the processing performed by the configuration of the block diagram described above. Then, the CPU 102 outputs the processing result from an output unit 106 or transmits the processing result from a communication unit 108 as necessary via the input/output interface 110, for example, and records the processing result in the hard disk 105, and the like.

Note that the input unit 107 includes a keyboard, a mouse, and a microphone. Furthermore, the output unit 106 includes a liquid crystal display (LCD) and a speaker.

Here, in the present specification, the processing performed by the computer according to the program does not necessarily need to be performed in time series in the order described as the flowcharts. That is, the processing performed by the computer according to the program also includes processing executed in parallel or individually (for example, parallel processing or processing by an object).

Furthermore, the program may be processed by one computer (processor), or may be processed by a plurality of computers in a distributed manner. Moreover, the program may be transferred to a remote computer and executed.

Moreover, in the present specification, a system means a set of a plurality of components (such as devices and modules (parts)), and it does not matter whether or not all the components are in the same housing. Thus, a plurality of devices housed in separate housings and connected via a network, and one device in which a plurality of modules is housed in one housing are both systems.

Furthermore, for example, a configuration described as one device (or a processing unit) may be divided so as to be configured as a plurality of devices (or processing units). Conversely, a configuration described as a plurality of devices (or processing units) in the above may be integrated so as to be configured as one device (or one processing unit). Furthermore, as a matter of course, a configuration other than those described above may be added to the configurations of the respective devices (or the respective processing units). Moreover, a part of a configuration of a certain device (or processing unit) may be included in a configuration of another device (or another processing unit) as long as the configuration or operation of the system as a whole is maintained substantially unchanged.

Furthermore, for example, the present technology can have a configuration of cloud computing in which one function is shared and processed in cooperation by a plurality of devices via a network.

Furthermore, for example, the program described above can be executed in an optional device. In that case, it is sufficient if the device has a necessary function (function block or the like) and can obtain necessary information.

Furthermore, for example, each step described in the flowcharts described above can be executed by one device, or can be shared and executed by a plurality of devices. Moreover, in a case where a plurality of types of processing is included in one step, the plurality of types of processing included in the one step can be executed by one device, or can be shared and executed by a plurality of devices. In other words, a plurality of types of processing included in one step can also be executed as processing with a plurality of steps. Conversely, the processing described as a plurality of steps can also be integrated into one step to be executed.

Note that the program executed by the computer may be designed in such a manner that the processing of steps describing the program are executed in time series in the order described in the present specification, or may be individually executed in parallel or at a necessary timing such as on calling. That is, as long as there is no inconsistency, the processing of the respective steps may be executed in an order different from the order described above. Moreover, the processing of the steps describing the program may be executed in parallel with processing of another program, or may be executed in combination with processing of another program.

Note that, as long as there is no inconsistency, each of a plurality of the present technologies described in the present specification can be independently implemented alone. As a matter of course, it is also possible to implement a plurality of optional present technologies in combination. For example, a part or the whole of the present technology described in any of the embodiments can be implemented in combination with a part or the whole of the present technology described in another embodiment. Furthermore, a part or the whole of an optional one of the present technologies described above can be implemented in combination with another technology not described above.

<Application Example to Endoscopic Surgery System>

The technology according to the present disclosure (present technology) is applicable to various products. For example, the technology according to the present disclosure may be applied to an endoscopic surgery system.

Figure 9:
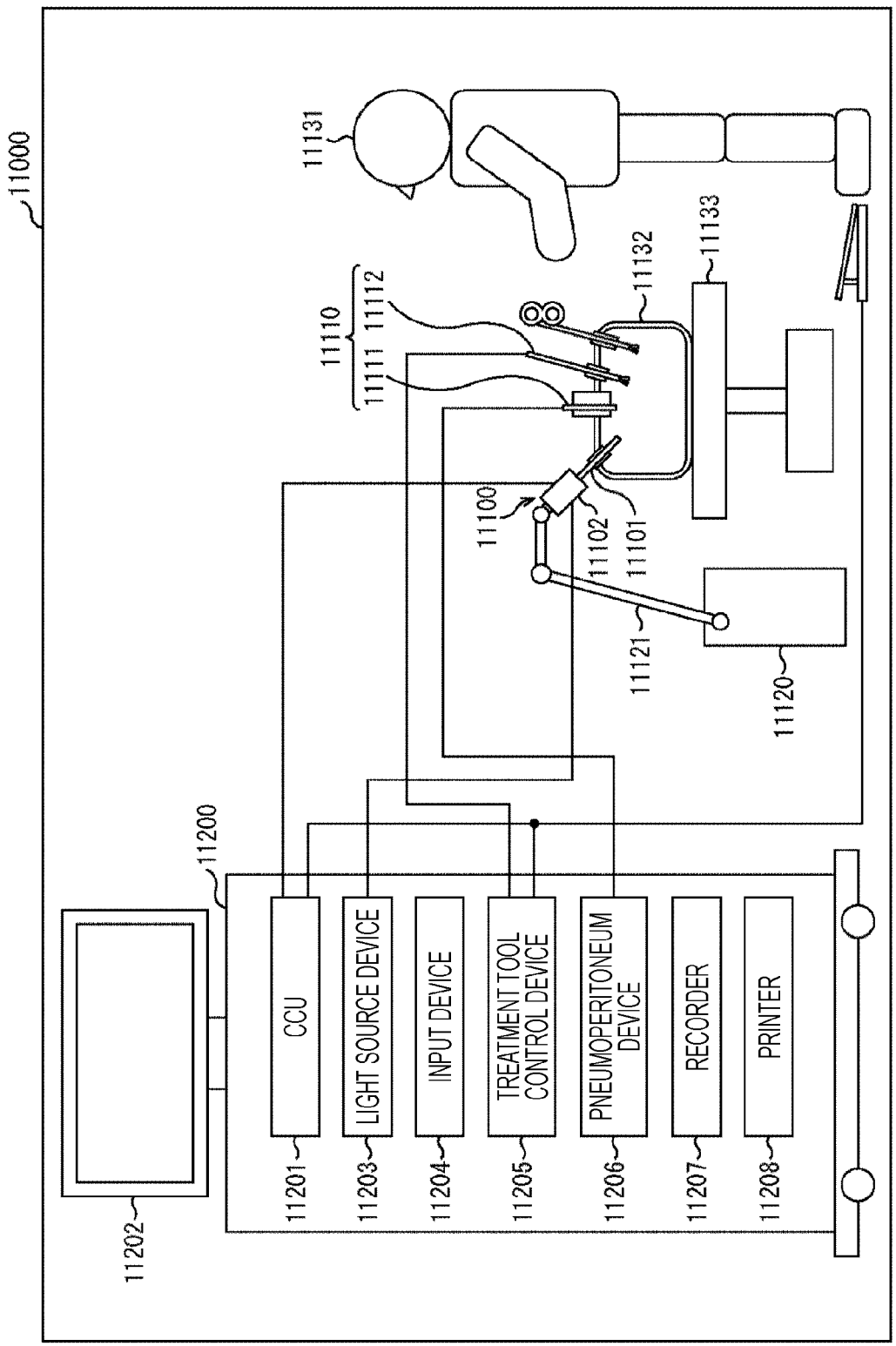
FIG. 9 is a diagram illustrating an example of a schematic configuration of an endoscopic surgery system.

FIG. 9 is a diagram illustrating an example of a schematic configuration of an endoscopic surgery system to which the technology according to the present disclosure (present technology) can be applied.

FIG. 9 illustrates an operator (doctor) 11131 performing surgery on a patient 11132 on a patient bed 11133 by using an endoscopic surgery system 11000. As illustrated, the endoscopic surgery system 11000 includes an endoscope 11100, other surgical tools 11110 such as a pneumoperitoneum tube 11111 and an energy treatment tool 11112, a support arm device 11120 that supports the endoscope 11100, and a cart 11200 on which various devices for an endoscopic surgery are mounted.

The endoscope 11100 includes a lens barrel 11101 in which a region having a predetermined length from a tip is inserted into a body cavity of the patient 11132, and a camera head 11102 connected to a base end of the lens barrel 11101. In the illustrated example, the endoscope 11100 configured as a so-called rigid mirror having the rigid lens barrel 11101 is illustrated. However, the endoscope 11100 may be configured as a so-called flexible mirror having a flexible lens barrel.

At the tip of the lens barrel 11101, an opening into which an objective lens is fitted is provided. A light source device 11203 is connected to the endoscope 11100, and light generated by the light source device 11203 is guided to the tip of the lens barrel by a light guide extending inside the lens barrel 11101, and is emitted through the objective lens toward an object to be observed in the body cavity of the patient 11132. Note that the endoscope 11100 may be a forward-viewing endoscope, an oblique-viewing endoscope, or a side-viewing endoscope.

An optical system and an image sensor are provided inside the camera head 11102, and reflected light (observation light) from the object to be observed is collected on the image sensor by the optical system. The observation light is photoelectrically converted by the image sensor to generate an electrical signal corresponding to the observation light, that is, an image signal corresponding to an observation image. The image signal is transmitted as RAW data to a camera control unit (CCU) 11201.

The CCU 11201 includes a central processing unit (CPU) and a graphics processing unit (GPU), and integrally controls operations of the endoscope 11100 and a display device 11202. Moreover, the CCU 11201 receives an image signal from the camera head 11102 and performs, on the image signal, for example, various types of image processing for displaying an image based on the image signal, such as development processing (demosaicing processing).

Under the control of the CCU 11201, the display device 11202 displays an image based on an image signal subjected to image processing by the CCU 11201.

The light source device 11203 includes, for example, a light source such as a light emitting diode (LED), and supplies the endoscope 11100 with irradiation light at the time of imaging a surgical site and the like.

An input device 11204 is an input interface to the endoscopic surgery system 11000. A user can input various types of information and an instruction to the endoscopic surgery system 11000 via the input device 11204. For example, a user inputs an instruction to change an imaging condition (a type of irradiation light, a magnification, a focal length, and the like), or the like by the endoscope 11100.

A treatment tool control device 11205 controls driving of the energy treatment tool 11112 for ablation of tissue, incision, sealing of a blood vessel, and the like. A pneumoperitoneum device 11206 delivers gas into a body cavity of the patient 11132 via the pneumoperitoneum tube 11111 in order to inflate the body cavity, for the purpose of securing a field of view by the endoscope 11100 and securing a working space for the operator. A recorder 11207 is a device capable of recording various types of information related to surgery. A printer 11208 is a device capable of printing various types of information related to surgery in various formats such as text, images, or graphs.

Note that the light source device 11203, which supplies the endoscope 11100 with irradiation light when imaging a surgical site, includes a white light source including an LED, a laser light source, or a combination thereof, for example. In a case where the white light source includes a combination of RGB laser light sources, output intensity and output timing of each color (each wavelength) can be controlled with high accuracy, and thus a white balance of a captured image can be adjusted in the light source device 11203. Furthermore, in this case, it is also possible to capture images corresponding to R, G, and B in a time-division manner by irradiating an object to be observed with laser light from each of the RGB laser light sources in a time-division manner, and controlling driving of an image sensor of the camera head 11102 in synchronization with the irradiation timing. According to such a method, a color image can be obtained without providing the image sensor with a color filter.

Furthermore, driving of the light source device 11203 may be controlled to change intensity of light to be output every predetermined time. By controlling driving of an image sensor of the camera head 11102 in synchronization with the timing of changing the light intensity to acquire images in a time-division manner, and combining the images together, it is possible to generate a high dynamic range image without so-called underexposure and overexposure.

Furthermore, the light source device 11203 may be capable of supplying light in a predetermined wavelength band compatible with special light observation. In the special light observation, for example, so-called narrow band imaging is performed, in which an image of a predetermined tissue such as a blood vessel in a superficial portion of a mucous membrane is captured at a high contrast by emitting light in a narrow band compared to irradiation light during normal observation (that is, white light) by using wavelength dependency of light absorption by a body tissue. Alternatively, in the special light observation, fluorescent observation in which an image is obtained by fluorescent light generated by irradiation of excitation light may be performed. In the fluorescent observation, it is possible to, for example, irradiate a body tissue with excitation light to observe fluorescent light from the body tissue (autofluorescence observation), or locally inject a reagent such as indocyanine green (ICG) into a body tissue while also irradiating the body tissue with excitation light corresponding to a fluorescence wavelength of the reagent to obtain a fluorescent image. The light source device 11203 can be configured to be capable of supplying narrow-band light and/or excitation light corresponding to such special light observation.

Figure 10:
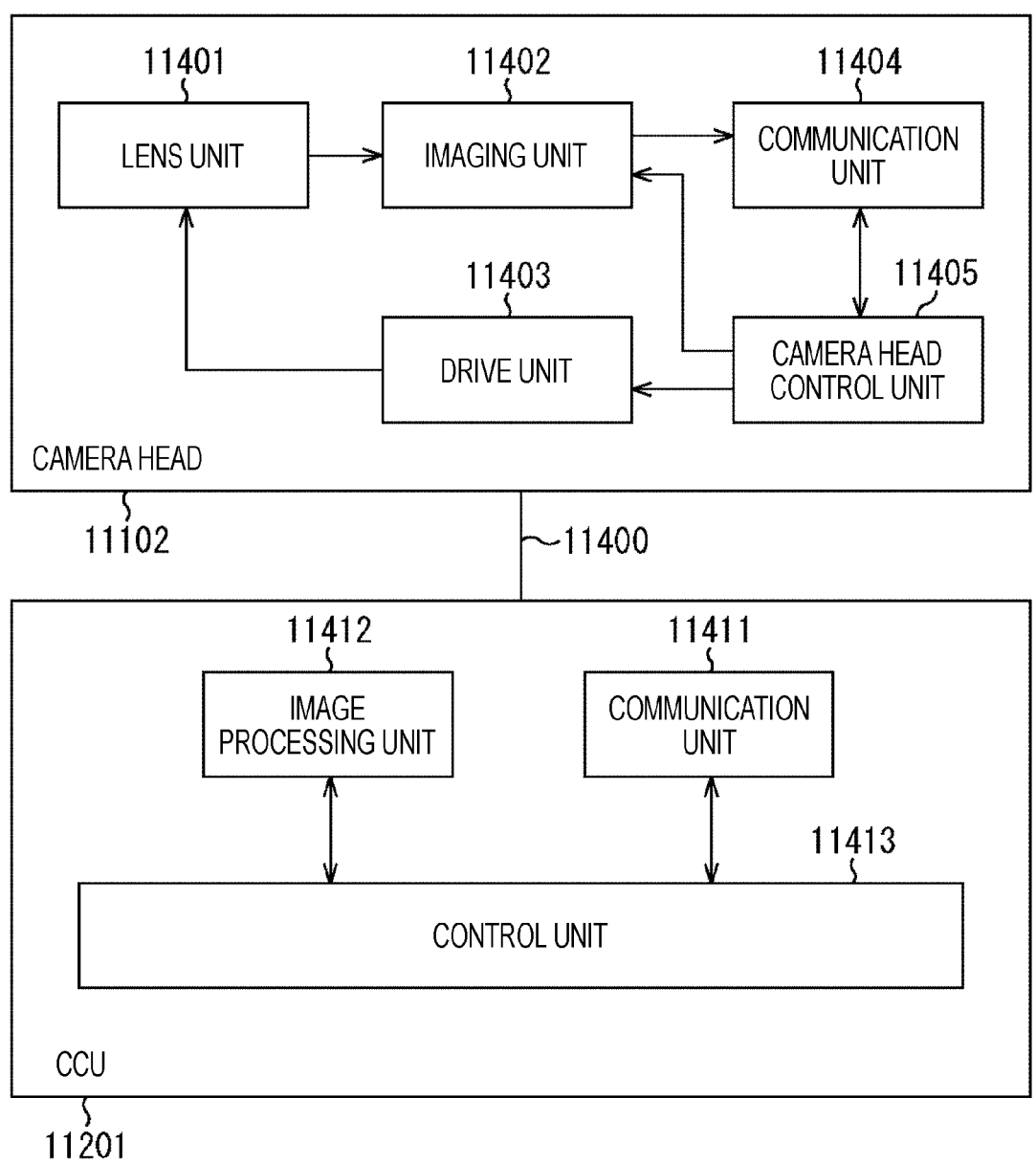
FIG. 10 is a block diagram illustrating an example of functional configurations of a camera head and a CCU.

FIG. 10 is a block diagram illustrating an example of functional configurations of the camera head 11102 and the CCU 11201 illustrated in FIG. 9.

The camera head 11102 includes a lens unit 11401, an imaging unit 11402, a drive unit 11403, a communication unit 11404, and a camera head control unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided at a connection portion with the lens barrel 11101. Observation light taken in from the tip of the lens barrel 11101 is guided to the camera head 11102 and enters the lens unit 11401. The lens unit 11401 includes a combination of a plurality of lenses including a zoom lens and a focus lens.

The number of image sensors constituting the imaging unit 11402 may be one (so-called single-plate type) or plural (so-called multi-plate type). In a case where the imaging unit 11402 is configured as that of the multi-plate type, for example, an image signal corresponding to each of R, G, and B may be generated by each image sensor and a color image may be obtained by combining the image signals. Alternatively, the imaging unit 11402 may include a pair of image sensors for acquiring image signals for a right eye and a left eye compatible with three-dimensional (3D) display. By performing the 3D display, the operator 11131 can more accurately grasp the depth of a biological tissue in a surgical site. Note that, in the case where the imaging unit 11402 is configured as that of a multi-plate type, a plurality of systems of lens units 11401 may be provided corresponding to the respective image sensors.

Furthermore, the imaging unit 11402 may not necessarily be provided in the camera head 11102. For example, the imaging unit 11402 may be provided inside the lens barrel 11101, just behind the objective lens.

The drive unit 11403 includes an actuator, and moves the zoom lens and the focus lens of the lens unit 11401 by a predetermined distance along an optical axis, under the control of the camera head control unit 11405. With this configuration, a magnification and a focus of a captured image by the imaging unit 11402 can be appropriately adjusted.

The communication unit 11404 includes a communication device for transmitting and receiving various types of information to and from the CCU 11201. The communication unit 11404 transmits, as RAW data, an image signal obtained from the imaging unit 11402 to the CCU 11201 via the transmission cable 11400.

Furthermore, the communication unit 11404 receives a control signal for controlling driving of the camera head 11102 from the CCU 11201 and supplies the control signal to the camera head control unit 11405. The control signal includes, for example, information related to imaging conditions such as information that a frame rate of a captured image is designated, information that an exposure value upon imaging is designated, and/or information that a magnification and a focus of a captured image are designated.

Note that the imaging conditions described above such as a frame rate, an exposure value, a magnification, and a focus may be designated appropriately by a user, or may be set automatically by the control unit 11413 of the CCU 11201 on the basis of an acquired image signal. In the latter case, a so-called auto exposure (AE) function, auto focus (AF) function, and auto white balance (AWB) function are mounted in the endoscope 11100.

The camera head control unit 11405 controls driving of the camera head 11102 on the basis of a control signal from the CCU 11201 received via the communication unit 11404.

The communication unit 11411 includes a communication device for transmitting and receiving various types of information to and from the camera head 11102. The communication unit 11411 receives an image signal transmitted from the camera head 11102 via the transmission cable 11400.

Furthermore, the communication unit 11411 transmits, to the camera head 11102, a control signal for controlling driving of the camera head 11102. An image signal and a control signal can be transmitted by telecommunication, optical communication, or the like.

The image processing unit 11412 performs various types of image processing on an image signal which is RAW data transmitted from the camera head 11102.

The control unit 11413 exercises various types of control related to imaging of a surgical site or the like by the endoscope 11100 and display of a captured image obtained by the imaging of the surgical site or the like. For example, the control unit 11413 generates a control signal for controlling driving of the camera head 11102.

Furthermore, the control unit 11413 causes the display device 11202 to display a captured image in which a surgical site or the like is captured, on the basis of an image signal subjected to image processing by the image processing unit 11412. At this time, the control unit 11413 may use various image recognition technologies to recognize various objects in the captured image. For example, by detecting the shape, color, and the like of an edge of an object included in the captured image, the control unit 11413 can recognize a surgical tool such as a forceps, a specific biological site, bleeding, mist during usage of the energy treatment tool 11112, and the like. When causing the display device 11202 to display the captured image, the control unit 11413 may superimpose and display various types of surgical support information on the image of the surgical site by using the recognition result. The surgical support information is superimposed and displayed to be presented to the operator 11131, so that a burden on the operator 11131 can be reduced and the operator 11131 can reliably proceed with surgery.

The transmission cable 11400 that connects the camera head 11102 and the CCU 11201 is an electrical signal cable compatible with communication of an electrical signal, an optical fiber compatible with optical communication, or a composite cable of the electrical signal cable and the optical fiber.

Here, in the illustrated example, communication is performed wiredly by using the transmission cable 11400, but communication between the camera head 11102 and the CCU 11201 may be performed wirelessly.

An example of the endoscopic surgery system to which the technology according to the present disclosure can be applied has been described above. The technology according to the present disclosure can be applied to the image processing unit 11412 of the CCU 11201 among the configurations described above. In addition, by applying the technology according to the present disclosure to the image processing unit 11412 of the CCU 11201, it is possible to output an image in which a blur has been appropriately corrected. Thus, it is possible for an operator to reliably confirm a surgical site.

Note that, although the endoscopic surgery system has been described as an example here, the technology according to the present disclosure may be applied to other systems, for example, a microscopic surgery system.

<Combination Example of Configurations>

Note that the present technology can also include the following configurations.

(1)

An endoscopic surgery system including:
a motion estimation unit that estimates motion components at a time of imaging on the basis of an image captured by an endoscope, and sets a degree of reliability indicating a degree that the motion components are motion components for the entire image; and
a correction amount control unit that controls, according to the degree of reliability, a correction amount used when correction processing of correcting a blur is performed on the image.

(2)

The endoscopic surgery system according to (1), in which
the motion estimation unit estimates which of a single motion component largely occupied by motion components of a single size and direction or a plurality of motion components largely occupied by motion components of a plurality of different sizes and directions is included in the image.

(3)

The endoscopic surgery system according to (2), in which
the motion estimation unit sets a first value as the degree of reliability in a case where it is estimated that the image includes a single motion component, and sets a second value as the degree of reliability in a case where it is estimated that the image includes a plurality of motion components.

(4)

The endoscopic surgery system according to (3), in which
the first value is 1.0, and
the second value is 0.0.

(5)

The endoscopic surgery system according to (3), further including
an operation unit that calculates, on the basis of a local motion vector indicating a local motion of the image, a norm and an angle of a plurality of the local motion vectors, and calculates a norm standard deviation of the local motion vector group and an angle standard deviation of the local motion vector group,
in which the motion estimation unit refers to a predetermined threshold, and estimates the motion components included in the image on the basis of the norm standard deviation and the angle standard deviation.

(6)

The endoscopic surgery system according to (5), in which
the motion estimation unit
refers to a threshold curve represented by the threshold with the norm standard deviation as a vertical axis and the angle standard deviation as a horizontal axis,
estimates, in a case where the norm standard deviation and the angle standard deviation obtained from the image are in a region less than the threshold curve, that the image includes a single motion component, and sets the first value as the degree of reliability, and
estimates, in a case where the norm standard deviation and the angle standard deviation obtained from the image are in a region equal to or larger than the threshold curve, that the image includes a plurality of motion components, and sets the second value as the degree of reliability.

(7)

The endoscopic surgery system according to (5), in which
the motion estimation unit
refers to a first threshold curve and a second threshold curve represented by the threshold with the norm standard deviation as a vertical axis and the angle standard deviation as a horizontal axis,
estimates, in a case where the norm standard deviation and the angle standard deviation obtained from the image are in a region less than the threshold curve, that the image includes a single motion component, and sets the first value as the degree of reliability,
sets, in a case where the norm standard deviation and the angle standard deviation obtained from the image are in a region equal to or larger than the first threshold curve and equal to or smaller than the second threshold curve, a value from the first value to the second value as the degree of reliability, and
estimates, in a case where the norm standard deviation and the angle standard deviation obtained from the image are in a region larger than the threshold curve, that the image includes a plurality of motion components, and sets the second value as the degree of reliability.

(8)

The endoscopic surgery system according to any one of (1) to (7), in which
the correction amount control unit accumulates the degree of reliability sequentially supplied from the motion estimation unit, and controls the correction amount by using the degree of reliability smoothed in a time direction.

(9)

The endoscopic surgery system according to (5), further including:
a feature point extraction unit that extracts a feature point to be a point indicating a portion to be a feature in the image; and
a local motion vector detection unit that detects the local motion vector on the basis of motions of a plurality of the feature points detected by the feature point extraction unit.

(10)

The endoscopic surgery system according to (9), further including
a global motion amount estimation unit that estimates a global motion amount indicating an overall motion of the image on the basis of a plurality of the local motion vectors,
in which the correction amount control unit obtains the correction amount on the basis of the global motion amount.

(11)

The endoscopic surgery system according to any one of (1) to (10), further including
a correction processing unit that performs the correction processing on the image according to the correction amount controlled by the correction amount control unit.

(12)

An image processing apparatus including:
a motion estimation unit that estimates motion components at a time of imaging on the basis of an image captured by an endoscope, and sets a degree of reliability indicating a degree that the motion components are motion components for the entire image; and a correction amount control unit that controls, according to the degree of reliability, a correction amount used when correction processing of correcting a blur is performed on the image.

(13) An image processing method performed by an image processing apparatus, the image processing method including:

estimating motion components at a time of imaging on the basis of an image captured by an endoscope, and setting a degree of reliability indicating a degree that the motion components are motion components for the entire image; and controlling, according to the degree of reliability, a correction amount used when correction processing of correcting a blur is performed on the image.

Note that the present embodiment is not limited to the embodiments described above, and various modifications can be made without departing from the gist of the present disclosure. Furthermore, the effects described in the present specification are merely examples and are not limitative, and other effects may be achieved.

REFERENCE SIGNS LIST

11 Endoscopic surgery system
12 Endoscope
13 Energy treatment tool
14 Display device
15 Device unit
16 Forceps
21 Image processing unit
22 Feature point extraction unit
23 Local motion vector detection unit
24 Global motion amount estimation unit
25 Operation unit
26 Motion estimation unit
27 Correction amount control unit
28 Correction processing unit

The invention claimed is:

1. An endoscopic surgery system, comprising:
an endoscope configured to capture an image;
a motion estimation unit configured to:
estimate one or more motion components at a time of the capture of the image, wherein the one or more motion components are estimated based on the captured; and
set, based on the estimated one or more motion components, a degree of reliability indicating that the estimated one or more motion components correspond to at least one of a motion of the endoscope or a motion of a surgical tool;
a correction amount control unit configured to control a correction amount based on the degree of reliability; and
a correction processing unit configured to correct, based on the controlled correction amount, a blur associated with the captured image.

2. The endoscopic surgery system according to claim 1, wherein
the motion estimation unit is further configured to estimate whether the estimated one or more motion components include a single motion component or a plurality of motion components,
the single motion component has a single size and a single direction, and
the plurality of motion components has a plurality of different sizes and a plurality of different directions.

3. The endoscopic surgery system according to claim 2, wherein the motion estimation unit is further configured to:
set a first value as the degree of reliability based on the estimation that the one or more motion components include the single motion component; and
set a second value as the degree of reliability based on the estimation that the one or more motion components include the plurality of motion components.

4. The endoscopic surgery system according to claim 3, wherein
the first value is 1.0, and
the second value is 0.0.

5. The endoscopic surgery system according to claim 3, further comprising an operation unit configured to:
acquire a plurality of local motion vectors indicating a local motion of the captured image;
determine, based on the plurality of local motion vectors, each of a norm of the plurality of local motion vectors and an angle of the plurality of local motion vectors; and
determine, based on the determined norm and the determined angle, each of:
a norm standard deviation of the plurality of local motion vectors, and
an angle standard deviation of the plurality of local motion vectors, wherein the motion estimation unit is further configured to:
obtain a threshold; and
estimate the one or more motion components of the image based on each of the obtained threshold, the determined norm standard deviation, and the determined angle standard deviation.

6. The endoscopic surgery system according to claim 5, wherein the motion estimation unit is further configured to:
set, in a graph, a threshold curve that represents the threshold, wherein the graph includes the norm standard deviation as a vertical axis and the angle standard deviation as a horizontal axis;
estimate, in a case where the norm standard deviation and the angle standard deviation are in a first region of the graph, that the one or more motion components include the single motion component, wherein the first region is less than the threshold curve;
set the first value as the degree of reliability based on the estimation that the one or more motion components include the single motion component;
estimate, in a case where the norm standard deviation and the angle standard deviation are in a second region of the graph, that the one or more motion components include the plurality of motion components, wherein the second region is one of equal to or larger than the threshold curve; and
set the second value as the degree of reliability based on the estimation that the one or more motion components include the plurality of motion components.

7. The endoscopic surgery system according to claim 5, wherein the motion estimation unit is further configured to:
set, in a graph, each of a first threshold curve and a second threshold curve, wherein
at least one of the first threshold curve and the second threshold curve represents the threshold, and
the graph includes the norm standard deviation as a vertical axis and the angle standard deviation as a horizontal axis;

estimate, in a case where the norm standard deviation and the angle standard deviation are in a first region, that the one or more motion components include the single motion component, wherein the first region is less than the first threshold curve;

set the first value as the degree of reliability based on the estimation that the one or more motion components include the single motion component:

set, in a case where the norm standard deviation and the angle standard deviation are in a second region of the graph, a third value, from the first value to the second value, as the degree of reliability, wherein the second region is each of:

one of equal to or larger than the first threshold curve, and one of equal to or smaller than the second threshold curve;

estimate, in a case where the norm standard deviation and the angle standard deviation are in a third region of the graph, that the one or more motion components include the plurality of motion components, wherein the third region is larger than the second threshold curve; and set the second value as the degree of reliability based on the estimation that the one or more motion components include the plurality of motion components.

8. The endoscopic surgery system according to claim 5, further comprising:

a feature point extraction unit configured to extract a plurality of feature points from the captured image, wherein each feature point of the plurality of feature points indicates a portion of the image, and the portion of the image indicates a feature of the captured image; and a local motion vector detection unit configured to detect the plurality of local motion vectors based on a plurality of motions of the extracted plurality of feature points.

9. The endoscopic surgery system according to claim 8, further comprising a global motion amount estimation unit configured to estimate a global motion amount indicating an overall motion of the captured image, wherein the global motion amount is estimated based on the plurality of local motion vectors, and the correction amount control unit is further configured to obtain the correction amount based on the global motion amount.

10. The endoscopic surgery system according to claim 1, wherein the motion estimation unit is further configured to sequentially transmit the degree of reliability to the correction amount control unit, and the correction amount control unit is further configured to:

accumulate the sequentially transmitted degree of reliability;

smooth the accumulated degree of reliability in a time direction; and control the correction amount based on the smoothed degree of reliability.

11. The endoscopic surgery system according to claim 1, wherein the correction processing unit is further configured to:

execute a correction process on the captured image based on the controlled correction amount; and correct the blur based on the execution of the correction process.

12. The endoscopic surgery system according to claim 1, wherein the surgical tool corresponds to at least one of an energy treatment tool or a forceps.

13. An image processing apparatus, comprising:

a motion estimation unit configured to:

acquire an image from an endoscope, wherein the endoscope captures the image;

estimate one or more motion components at a time of the capture of the image, wherein the one or more motion components are estimated based on the acquired; and set, based on the estimated one or more motion components, a degree of reliability indicating that the estimated one or more motion components correspond to at least one of a motion of the endoscope or a motion of a surgical tool;

a correction amount control unit configured to control a correction amount based on the degree of reliability; and a correction processing unit configured to correct, based on the controlled correction amount, a blur associated with the acquired image.

14. An image processing method, comprising:

in an image processing apparatus:

acquiring an image from an endoscope, wherein the endoscope captures the image;

estimating one or more motion components at a time of the capture of the image, wherein the one or more motion components are estimated based on the acquired image;

setting, based on the estimated one or more motion components, a degree of reliability indicating that the estimated one or more motion components correspond to at least one of a motion of the endoscope or a motion of a surgical tool;

controlling a correction amount based on the degree of reliability; and correcting, based on the controlled correction amount, a blur associated with the acquired image.

15. An endoscopic surgery system, comprising:

an endoscope configured to capture an image;

a motion estimation unit configured to:

estimate one or more motion components at a time of the capture of the image, wherein the one or more motion components are estimated based on the captured image;

set, based on the estimated one or more motion components, a degree of reliability indicating that the estimated one or more motion components correspond to at least one of a motion of the endoscope or a motion of a surgical tool; and sequentially transmit the degree of reliability;

a correction amount control unit configured to:

accumulate the sequentially transmitted degree of reliability;

smooth the accumulated degree of reliability in a time direction; and control a correction amount based on the smoothed degree of reliability; and a correction processing unit configured to correct, based on the controlled correction amount, a blur associated with the captured image.

\* \* \* \* \*